United States Patent [19]

Christie

[11] Patent Number: 5,346,830
[45] Date of Patent: Sep. 13, 1994

[54] GENE EXPRESSION SYSTEM BASED ON REGULATORY ELEMENTS OF BATERIOPHAGE P2 AND SATELLITE PHAGE P4

[75] Inventor: Gail Christie, Richmond, Va.

[73] Assignee: The Center for Innovative Technology, Herndon, Va.

[21] Appl. No.: 28,730

[22] Filed: Mar. 8, 1993

Related U.S. Application Data

[63] Continuation of Ser. No. 714,141, Jun. 11, 1991, abandoned.

[51] Int. Cl.$^5$ .............. C12N 15/70; C12N 1/21; C12N 15/11; C12N 15/31
[52] U.S. Cl. ............... 435/320.1; 435/252.33; 536/23.7; 536/24.1
[58] Field of Search ............... 435/69.1, 320.1, 252.33; 536/23.7, 24.1

[56] References Cited

PUBLICATIONS

Suzuki et al. (1986), An Introduction to Genetic Analysis, Third Edition, (W. H. Freeman & Co., New York) pp. 385–392.

Slonczewski et al. (Jul. 1987), J. Bacteriol., vol. 169(7), pp. 3001–3006.

Souza, L., et al., "A Transactivation Mutant of Satellite Phage P4," Virology 81:81–90 (1977).

Studier, F. W. and B. A. Moffatt, "Use of Bacteriophage T7 RNA Polymerase to Direct Selective High-Level Expression of Cloned Genes," J. Mol. Biol. 189:113–130 (1986).

Grambow, N. J., et al., "Deletion Analysis of a Bacteriophage P2 Late Promoter," Gene 95:9–15 (1990).

Christie, G. E. and R. Calendar, "Interactions Between Satellite Bacteriophage P4 and Its Helpers," Annu. Rev. Genet. 24:465–490 (1990).

Primary Examiner—Richard A. Schwartz
Assistant Examiner—Philip W. Carter
Attorney, Agent, or Firm—Whitham, Curtis, Whitham & McGinn

[57] ABSTRACT

An *E. coli* heterologous gene expression system comprising a multicopy expression vector comprising an F promoter from bacteriophage P2; and at least one copy of a DNA sequence comprising a delta gene from satellite P4 operably linked to a regulatable promoter on a different replicon is disclosed.

2 Claims, No Drawings

GENE EXPRESSION SYSTEM BASED ON REGULATORY ELEMENTS OF BATERIOPHAGE P2 AND SATELLITE PHAGE P4

This application is a continuation of U.S. application Ser. No. 07/714,141, filed Jun. 11, 1991, now abandoned.

FIELD OF THE INVENTION

This invention relates to the control of heterologous gene expression in *E. coli* through the use of a positively activated promoter.

BACKGROUND OF THE INVENTION

The number of control systems useful for expressing heterologous genes in *E. coli* is somewhat limited. While it is difficult to predict or develop a system that will assuredly lead to high level expression of any targeted protein, there are a number of desirable characteristics that should be taken into account when designing an expression system. First, the promoter chosen to regulate heterologous gene expression should be easily and inexpensively induced in fermentation conditions. Second, an expression system should be tightly regulated since high level expression of a protein in *E. coli* may be detrimental or lethal to the cell. In addition, expression vectors should be designed with multiple cloning sites to facilitate subcloning of foreign genes and gene fragments.

High level expression of heterologous genes in bacteria can be achieved by using a tightly regulatable promoter such as the *E. coli* lac promoter (see, e.g. Backman, K. and M. Ptashne, (1978) "Maximizing gene expression on a plasmid using recombination in vitro." Cell 13:65–71); the trp promoter (see, e.g. Nichols, B. P. and C. Yanofsky, (1983) "Plasmids Containing the trp Promoters of *Escherichia coli* and *Serratia marcescens* and Their Use in Expressing Cloned Genes." Methods in Enzym. 101:155–164); the λ phage L promoter (See e.g. Rosenberg, M., et al. (1983) "The use of pKC30 and its Derivatives for Controlled Expression of Genes." Methods in Enzym. 101:123–138); and the T7 $\phi$10 promoter (See e.g. Studier, F. W. and B. A. Moffatt (1986). "Use of Bacteriophage T7 RNA Polymerase to Direct Selective High-level Expression of Cloned Genes." J. Mol. Biol. 189:113–130). All of these promoters, except for the T7 $\phi$10, are regulated by the presence or absence of their cognate repressor. Maintaining repression of these promoters when they are on multicopy or runaway plasmid replicons can be difficult. As a consequence, expensive or awkward procedures must be used to inactivate the repressor in these negatively regulated systems.

The T7 $\phi$10 promoter is activated in a positive fashion by the presence of the T7 polymerase. In the absence of the T7 polymerase, transcription from $\phi$10 promoters is very low. Since the T7 polymerase gene itself is located in the *E. coli* chromosome, in single copy and controlled by the *lac* repressor, its synthesis can be well controlled. This arrangement has the advantage of keeping the promoter inactive regardless of the promotor copy number, resulting in tighter regulation of the expression system.

The phage P2 contains four late operons encoding packaging and lysis genes. (See, e.g., Lindahi, G. (1971) "On the Control of Transcriptions in Bacteriophage P2." Virol. 46(3):620–633; Sunshine, M. G., et al. (1971) "P2 Phage Amber Mutants: Characterization by Use of a Polarity Suppressor." Virol: 46(3):691–702; and Geisselsolder, J. M., et at. (1973): "In Vivo Transcription Patterns of Template Coliphage P2" J. Mol. Biol. 77(3):425-415). Transcription of these operons, F,O,P and V, requires both *E. coli* RNA polymerase and the product of the P2 ogr gene (See, e.g. Lindqvist, B. H. (1974) "Expression of Phage Transcription in P2 Lysogens Infected with Helper-dependent Coliphage P4" Proc. Natl. Acad. Sci. USA 71(7):2770–2774; Sunshine, M. G. and B. Sauer, (1975) "A Bacterial Mutation Blocking P2 Phage Late Gene Expression." Proc. Natl. Acad. Sci. USA 72(7):2770–2774). Examination of the sequences of these late promoters has revealed the absence of a strong consensus *E. coli* promoter ($-35$ and $-10$ regions).

P4, a satellite virus of bacteriophage P2, does not encode its own morphogenic functions but can be supplied with them by a co-infecting P2 virion. (See e.g., Six, E. W. (1975) "The Helper Dependence of Satellite Bacteriophage P4: Which Gene Functions of Bacteriophage P2 are Needed by P4?" Virol.67:249-26). One of the late P4 proteins, $\delta$, can transactivate the P2 late promoters in a manner analogous to the P2 ogr protein. (See, e.g., Souza, L. (1977) "A Transactivation Mutant of Satellite Phage P4." Virol. 81:81–90). In addition, the $\delta$ protein can activate one of P4's own promoters (psid), which in turn encodes the delta gene (See, e.g. Dale, E. C. et al. (1986) "Organization and Expression of the Satellite Bacteriophage P4 Late Gene Cluster," J. Mol. Biol. 192:793–803).

The instant invention provides a novel tightly regulated high-level heterologous gene expression system for *E. coil* based on the principle of positive activation of a P2 F promoter by the regulatable expression of the P4 delta gene. The P2 F promoter, which is synthesized beginning at position $-70$, with respect to the start site of transcription, is cloned into a multicopy plasmid. *E. coli* RNA polymerase is activated to transcribe the F promoter by the P4 $\delta$ protein which is supplied, in a sufficient quantity, by a single or a few copies of the delta gene which is under control of a regulatable promoter in a lysogenic host. Accordingly, the present invention provides an inexpensive and tightly regulatable expression system useful to produce heterologous proteins in *E. coli* hosts.

INFORMATION DISCLOSURE

Souza, L. (1977), "A Transactivation Mutant of Satellite Phage P4." Virol 81:81–90 discloses that the $\delta$ protein of phage P4 can transactivate the P2 F promoter.

Studier, W. and B. Moffatt (1986) J. Mol. Bio. 189:113–130 disclose that a single copy of a gene coding for a positive regulatory element, T7 RNA polymerase, is sufficient to direct high-level transcription from a T7 promoter in a multicopy plasmid. Studier and Moffatt suggest that the T7 expression system should be capable of transcribing almost any gene in *E. coli* and that perhaps comparable T7 systems could be developed in other types of cells.

Grambow, N., et. al (1990), "Deletion Analysis of a Bacteriophage P2 Late Promoter" Gene 95:9–15, disclose that the sequence between nucleotides $-69$ and $-64$ from the transcription start point of the P2 F promoter is essential for promoter function.

Christie, G. (1990), "Interactions Between Satellite Bacteriophage P4 and its Helpers", Ann. Rev. Genet.

24:465–490 discloses the role of P2 as the helper for P4 lytic growth.

None of the above publications discloses that the delta gene and the P2 F promoter can be used in combination with the delta gene under the control of a regulatable promoter in *E. coli* to express heterologous genes as disclosed in the instant invention. In addition, none of the above publications discloses that the δ protein expressed from a promoter in the bacterial chromosome can transactivate the F promoter on a plasmid to express another gene.

SUMMARY OF THE INVENTION

The present invention relates to an *E. coli* heterologous gene expression system comprising a multicopy expression vector comprising an F promoter; and at least one copy of a DNA sequence comprising a delta gene operably linked to a regulatable promoter; and to a method of producing a heterologous protein in *E. coli*.

DETAILED DESCRIPTION OF THE INVENTION

The instant invention provides a novel heterologous gene expression system in *E. coli* which is based on positive activation of the P2 F promoter by the P4 δ protein. *E. coli* RNA polymerase is activated to transcribe heterologous genes under the control of the P2 F promoter by the regulated expression of the satellite phage P4 δ protein supplied in trans.

As used herein the symbol "δ" refers to the delta protein. The word "delta" refers to the delta gene.

As used herein, "heterologous gene" refers to a gene under the regulation of a P2 F promoter which is not P2 F.

As used herein, "replicon" is defined as a self replicating piece of DNA.

As used herein, "F promoter" is defined as any part of the P2 wild-type promotor sequence which is responsive to δ protein activation in *E. coli*.

As used herein, "multicopy expression vector" refers to cloning vehicles such as plasmids or bacteriophages which have been specifically modified so as to permit insertion of foreign DNA. They contain all the appropriate signals and elements necessary transcription of the inserted DNA in a suitable host. They are present in such a host in copy numbers of one or more. Examples of such vectors are widely known and readily available.

As used herein, "regulatable promoter" refers to a promoter which is activated or repressed for transcription in response to external conditions such as the presence or absence of molecular control elements (e.g. IPTG, tryptophane)or pH or temperature. Regulatable promoters generally and specific examples are widely known and readily available.

According to the present invention, the gene encoding δ is present in the system on one replicon while the F promoter is on another replicon. Only a small amount of P4 δ protein is necessary to interact with a large number of copies of the P2 F promoter. Expression of the delta gene is regulated by a tightly controlled expression system including a regulatable promoter. Generally, a single copy of the delta gene is present while the gene under control of the F promoter is present on a large number of multicopy plasmids. The regulatory control of the single copy of the delta gene allows for the control of a large number of copies of the heterologous gene of interest under the control of the F promoter on the multicopy pasmids. Expression of the heterologous gene is thus essentially dependent upon activation of a regulatable promoter, such as the lac or pH promoter, that controls delta expression. According to the present invention, the delta gene under the control of a regulatable promoter may be on a plasmid or integrated in the chromosome of the host.

The heterologous gene of interest is ligated to various cloning vehicles or vectors for use in transforming *E. coli*. The vectors contain DNA sequences necessary for the expression of heterologous gene of interest which are operatively linked thereto. The heterologous gene expression control sequences of the instant invention include the P2 F promoter or any other P2 or P4 promoter which are dependent upon the presence of the P4 δ protein for transcription.

The expression of the heterologous gene of interest under the control of the F promoter in the present invention is directed through the regulation of δ synthesis. To easily manipulate gene expression during large-scale *E. coli* fermentation, it is advantageous to have a switch that could be rapidly and inexpensively activated to control delta expression. An example of such switch is a promoter in which transcription is regulated by external pH is described in U.S. patent application Ser. No. 07/614,166, now abandoned, which is incorporated herein by reference. Other regulatable promoters which can control delta expression and consequently operate the F promoter are well known in the art and include the lac and trp promoter systems. One having ordinary skill in the art could choose from many different widely available regulatable promoters to control delta synthesis and practice the present invention.

It is also contemplated that the P2 ogr gene can be substituted for the P4 delta gene in the present invention since the P4 and P2 late transcription regulatory proteins appear to function interchangeably. P4 requires either the product of the P4 delta gene or the P2 ogr gene for lytic growth. Because P2 or deletion phages can grow in the presence of δ, the δ protein can be substituted for ogr in P2 multiplication.

According to one embodiment of the present invention, a fragment of DNA which is to be expressed is inserted at either the ClaI or BarnHi site into the expression vector of the invention which is designated as pP2F6. The pP2F6 plasmid contains the P2 F promoter. Insertion of coding sequences at the ClaI or BamHI site will result in such a coding sequence placed under the regulatory control of the P2 F promoter in pP2F6. The pP2F6 vector has been deposited in accordance with the requirements under the Budapest Treaty on the International Recognition of the Deposit of Microorganisms for the Purposes of Patent Procedure at the Agricultural Research Culture Collection, Northern Regional Research Center (NRRL), 1815 North University Street, Peoria, Ill. 61604 on May 17, 1991 under accession number B18825. Although standard methods are set out below, insertion can be accomplished by several other methods which are known to those skilled in the art. First, one can modify the ends of the DNA fragments of interest so that the ends contain the proper overhanging bases to be suitable for ligation to the ClaI or BarnHi sites in pP2F6. In the case of the ClaI site the proper overhanging bases are 5'CG and in case of the BamHI site, the proper overhanging bases are 5'GATC. The fragment that is ligated with pP2F6 and a recombinant plasmid containing the fragment of interest is identified using standard procedures. The other method is to make the ends of the fragment of interest and the ClaI or BamHI digested pP2F6 blunt ended using standard procedures and ligating the two together. Other techniques used herein are set forth in Sambrook, et al., Molecular Cloning: A Laboratory Manual, 2nd Ed. (1987), which is incorporated herein by reference.

Plasmid pP2F6 with a heterologous DNA insert is then used to transform *E. coli* that is either to be or already transformed with a vector containing the delta gene under the control of a regulatable promoter. Alternatively, the recombinant pP2F6 can be used to transform an *E. coli* strain that has a delta gene under the control of a regulatable promoter integrated into the bacterial chromosome. One example of such an *E. coli* strain is E1952 which contains the delta gene under the control of a pH regulatable promoter. E1952 has been deposited in accordance with the requirements under the Budapest Treaty on the International Recognition of the Deposit of Microorganisms for the Purposes of Patent Procedure at the Agricultural Research Culture Collection, Northern Regional Research Center (NRRL), 1815 North University Street, Peoria, Ill. 61604 on May 17, 1991 under accession number B18824.

EXAMPLE 1

Synthesis of the F promotor and its insertion into a plasmid to produce plasmid pP2F6.

The F promoter was synthesized using oligonucleotides and inserted into a multicopy vector. Using the sequence data set out in SEQ ID NO; 1, 2, 3 and 4, oligonucleotides were synthesized and purified using procedures known to those skilled in the art. SEQ ID NO: 2 and 3 were phosphorylated at their 5' ends. SEQ ID NO: 1 and 2 were annealed and 3 and 4 were annealed by incubating one of each pair in 10 mM Tris, 0.1 mM NaCI at 65° C. followed by slowly cooling, approximately 45 minutes, to room temperature. The oligonucleotide pairs were then ligated together and the resulting product was electrophoresed through a 5% acrylamide gel. The product, corresponding to a DNA chain consisting of the 4 oligonucleotides set out in SEQ ID NO: 1, 2, 3 and 4, was purified from the gel and ligated to an EcoRI-BamHI fragment from plasmid pSRlac. The resulting plasmid, pP2F6, contains the pBR322 origin of replication, bla gene which encodes resistance to ampicillin, and a lacZ gene downstream from the F promoter such that maximal expression of lacZ is dependent on F promoter activity. The sequence of the F promoter may be modified so long as such modified sequences are still responsive to δ protein. The pP2F6 vector has been deposited in accordance with the requirements under the Budapest Treaty on the International Recognition of the Deposit of Microorganisms for the Purposes of Patent Procedure at the the Agricultural Research Culture Collection, Northern Regional Research Center (NRRL), 1815 North University Street, Peoria, Ill. 61604 on May 17, 1991 under accession number B18825.

EXAMPLE 2

Isolation of the Delta Gene

The phage P4 delta gene was isolated from phage P4 genomic DNA by digestion of the DNA with BamI and HpaI. The resulting fragment was missing the beginning of the delta coding region. The missing part of the delta coding region was supplied with the synthetic oligonucleotides set out as SEQ ID NO: 5 and SEQ ID NO: 6. SEQ ID NO: 5 and SEQ ID NO: 6 were annealed and mixed with pSRlac which was digested with ClaI and BarnHi and the BanI-HpaI DNA fragment containing the delta coding region. The mixture was ligated and a plasmid designated placdelta1-121 was isolated. Plasmid placdelta1-121 contains the delta gene under control of the lac promoter. A fragment of DNA containing the lac promoter and the entire delta gene can be excised from placdelta1-121 with EcoRI and BamHI.

The delta gene may be supplied by other methods. In example 3, the gene is supplied by λdelta-1. In addition, delta, without its promoter, can be taken from placdelta1-121 and placed downstream from any promoter in the chromosome. For example, the delta gene can be placed downstream from the pH promoter.

EXAMPLE 3

Lysogenization

Plasmid placdelta1-12 1 was digested with EcoRI and BamHi and a fragment containing the lac promoter and the delta gene was purified and ligated with EcoRI-BamHI digested pRS551 (Simons, R. et al, "Improved single and multicopy lac-based cloning vectors for protein and operon fusions." (1987) Gene 53:85-96) resulting in pRSdelta-1. Recombination between pRSdelta-1 and λRS45 (Simons et al, supra) was accomplished as described in Simons, et al, supra. A phage designated as λRSdelta-1, was identified from this recombination and was used to lysogenize an *E. coli* strain.

Lysogenization by λRSdelta-1 was performed as described in Arber, W. et al, 1983, p.450 in Lambda II, edited by Hendrix, R. et al, Cold Spring Harbor Laboratory, Cold Spring Harbor, N.Y. One of the resulting lysogens which is lac⁻, was designated as E1709. E1709, an *E. coli* strand carrying the delta gene, has been deposited at The Agricultural Research Culture Collection (NRRL), North Regional Research Center, 1815 North University Street, Peoria, Ill. 61604. under Accession No. B-18810 on Apr. 10, 1991.

EXAMPLE 4

Expression of lacZ gene in pP2F6

The lacZ gene was excised from plasmid pRS415 (Simons et al, supra) by digestion with SmaI and NruI resulting in a fragment with blunt ends and carrying the lacZ, lacY and part of the lacA genes. Plasmid pP2F6 was digested with BamHi and made blunt ended with nucleotides and Klenow enzyme using standard procedures. The lacZYA fragment and the treated pP2F6 were ligated together, used to transform *E. coli* DH5alpha (Life Technologies Inc., Gaithersburg, Md.) and plated onto LB plates containing 100 μg ampicillin/ml and 40 μg 5-bromo-4-chloro-3-indolyl-B-D-galactoside per ml. Colonies that were light blue were purified. The plasmid DNA from them was isolated and analyzed by DNA sequencing procedures. A plasmid with the lacZYA gene next to the F promoter, pP2F6lacZ, was identified and used to transform E1709, an *E. coli* strain that has the lacZYA genes deleted and carries λRSdelta-1.

E1709/pP2F6lacZ was grown in LB at 37° C. to an optical density at 550 nm of 0.1. Half of the culture was removed to another flask and isopropylthio-β-galactoside (IPTG) was added to a final concentration of 1 mM. The two cultures (+ and − IPTG) were incubated for 2 hours at 37° C. followed by β-galactosidase assay as described by Miller, J., Experiments in Molecular Genetics, (1972), Cold Spring Harbor Laboratories, Cold Spring Harbor, N.Y. Levels of β-galactosidase in cultures without IPTG were between 10 and 100 units. Levels of β-galactosidase in cultures to which IPTG was added were between 15,000 and 25,000. Thus, expression of the heterologous gene, in this case, lacZ, was dependent on transcription from the synthesized F promoter and expression of the delta gene in λRSdelta-1.

EXAMPLE 5

Integration of Delta Downstream From a pH Regulated Promoter

The source of the pH regulated promoter, as described in U.S. patent application, Ser. No. 07/614,166 was an *E. coli* strain, JLS8602 (Slonczewski, J. et al. (1987) "Mu-d directed lacZ fusions regulated by low pH *Escherichia coli*. J. Bacteriol. 169(7):3001–3006) which contains a Mu-d fusion in an operon that is induced when the pH of the medium is shifted from 7.6 to 5.8. A DNA fragment from this strain, as well as overlapping fragments from *E. coli* W3110, were used to provide homologous DNA for recombination of the delta gene into the chromosome downstream from the promoter. A DNA fragment containing a promoterless delta gene, which was isolated from pB9δ, and a chloramphenicol resistance gene (cml), was placed downstream from the pH promoter on a plasmid vector. The pB9δ plasmid was constructed by ligation of a blunt-ended fragment containing the delta gene isolated from SphI-EcoRI digested pUCδ-20 into the filled-in HindIII site of pBR329. The plasmid vector, pPHP6, contains the pH promoter region upstream from lacZYA. A 1.7 kb HindII fragment containing delta and a promoterless chloramphenicol resistance gene was gel-isolated from pB9δ and ligated with SimaI-digested pPHP6. JM101 was transformed with the ligated mixture and transformants were selected by resistance to chloramphenicol and ampicillin. The three generated transformants were purified. Plasmid DNA was isolated and analyzed by restriction digestion for the presence of the δ-cml fragment. The isolate which contained the correct sized insert was designated as pPHδC-3.

The δ-cml cassette was genetically crossed from pPHδC-3 to λA1-4. λA1-4 is a cI deleted, att deleted phage that contains the chromosomal Mu-d junction from JLS8602. The resulting phage, called λpHδC-4, was used to insert the δ-cml region into the chromosome downstream from the pH promoter. JLS8602 was infected with UV-irradiated λpHδC-4 and $Cm^R$ colonies were isolated. One of these colonies, which is called E1952, was shown by complementation of a P2 $ogr^-$ phage mutant, to make δ at pH 5.8. E1952 has been deposited at NRRL on May 17, 1991 and has been given accession number B18824.

E1952 was transformed with plasmid pP2F6lacZ. The level of β-galactosidase activity was examined when expression of the delta gene was controlled by the pH promoter. The level of β-galactosidase in E1952 containing pP2F6lacZ when the external pH is shifted to 5.8 was comparable to that observed in the E1709/pP2F6 in the presence of IPTG, around 20,000 units. The uninduced level (cells grown at pH 7.6) was around 500 units in E1952/pP2F6lacZ.

---

We claim:

1. An *E. coli* heterologous gene expression system comprising:
    a) a multicopy expression vector comprising an F promoter from bacteriophage P2; and
    b) at least one copy of a DNA sequence comprising a delta gene from satellite bacteriophage P4 operably linked to a regulatable promoter.

2. An *E. coli* heterologous gene expression system according to claim 1 further comprising a heterologous gene linked to said F promoter from bacteriophage P2.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AATTCGGGTT  GTGCTGTCGA  TTAGCCAACC  GGGACAAATA  GCCTGACATC  TCCGGCGCAA    60

CTGAAAATA                                                                 69
```

( 2 ) INFORMATION FOR SEQ ID NO:2:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GGGTGAGTGG  TATTTTCAGT  TGCGCCGGAG  ATGTCAGGCT  ATTTGTCCCG  GTTGGCTAAT    60

CGACAGCACA  ACCCG                                                         75
```

( 2 ) INFORMATION FOR SEQ ID NO:3:

( i ) SEQUENCE CHARACTERISTICS:
        ( A ) LENGTH: 67 base pairs
        ( B ) TYPE: nucleic acid -continued (C) STRANDEDNESS: single
(D) TOPOLOGY: linear (x i) SEQUENCE DESCRIPTION: SEQ ID NO:3:

```
CCACTCACCC ATTAACCTCT AGATTATTAA AAATTAAAGA GGTATATCGA TAATGAGTGA     60
CTATCAG                                                               67
```

(2) INFORMATION FOR SEQ ID NO:4:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (x i) SEQUENCE DESCRIPTION: SEQ ID NO:4:

```
GATCCTGATA GTCACTCATT ATCGATATAC CTCTTTAATT TTTAATAATC TAGAGGTTAA     60
T                                                                     61
```

(2) INFORMATION FOR SEQ ID NO:5:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (x i) SEQUENCE DESCRIPTION: SEQ ID NO:5:

```
CGATAATGAT TTACTGTCCG TCGTGTGGAC ATGTTGCTCA CACCCGTCGC GCACATTTCA     60
TGGACGATG                                                             69
```

(2) INFORMATION FOR SEQ ID NO:6:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (x i) SEQUENCE DESCRIPTION: SEQ ID NO:6:

```
GTGCCATCGT CCATGAAATG TGCGCGACGG GTGTGAGCAA CATGTCCACA CGACGGACAG     60
TAAATCATTA T                                                          71
```

(2) INFORMATION FOR SEQ ID NO:7:

(i) SEQUENCE CHARACTERISTICS:
        (A) LENGTH: 141 base pairs
        (B) TYPE: nucleic acid
        (C) STRANDEDNESS: double
        (D) TOPOLOGY: linear (x i) SEQUENCE DESCRIPTION: SEQ ID NO:7:

```
AATTCGGGTT GTGCTGTCGA TTAGCCAACC GGGACAAATA GCCTGACATC TCCGGCGCAA     60
CTGAAAATAC CACTCACCCA TTAACCTCTA GATTATTAAA AATTAAAGAG GTATATCGAT    120
AATGAGTGAC TATCAGGATC C                                              141
```